United States Patent [19]

Lachman et al.

[11] Patent Number: 5,343,258
[45] Date of Patent: Aug. 30, 1994

[54] SAFETY GLASSES

[76] Inventors: Leigh J. Lachman, 17 Stratford Dr., Livingston, N.J. 07039; Reid A. Lachman, 6 Robin Ct., Morristown, N.J. 07960

[21] Appl. No.: 11,885

[22] Filed: Feb. 1, 1993

[51] Int. Cl.$^5$ .......................... G02C 1/00; A61F 9/00
[52] U.S. Cl. ................................ 351/41; 351/57; 351/158; 2/431; 2/439; 2/440; 128/858; 359/511
[58] Field of Search ............... 2/431, 439, 440; 128/4, 128/858; 351/41, 57, 158; 359/509, 511

[56] References Cited

U.S. PATENT DOCUMENTS

| | | | |
|---|---|---|---|
| 1,247,853 | 11/1917 | McWenie | 351/45 |
| 1,424,848 | 8/1922 | Paddison | 351/158 |
| 1,637,406 | 8/1927 | Brumder | 2/432 |
| 1,844,232 | 2/1932 | Tharp | 2/13 |
| 2,003,379 | 6/1935 | Malcom | 2/439 |
| 2,139,275 | 12/1938 | Lee | 2/13 |
| 3,449,043 | 6/1969 | Houston | 351/41 |
| 3,592,525 | 7/1971 | Schultz | 351/41 |
| 4,364,645 | 12/1982 | Feinbloom | 351/158 |
| 4,429,959 | 2/1984 | Walters | 351/57 |
| 4,714,329 | 12/1987 | Hellström | 351/158 |
| 4,834,068 | 5/1989 | Gottesman | 128/4 |
| 4,848,322 | 7/1989 | Dash et al. | 128/4 |
| 4,958,623 | 9/1990 | Rocco | 128/7 |
| 4,976,254 | 12/1990 | Dash et al. | 128/4 |
| 5,088,809 | 2/1992 | Portney | 351/41 |
| 5,129,717 | 7/1992 | Feinbloom | 351/158 |

FOREIGN PATENT DOCUMENTS

| | | | |
|---|---|---|---|
| 825917 | 12/1937 | France | 351/41 |
| 844346 | 7/1939 | France | 351/41 |
| 1330277 | 10/1963 | France | . |
| 427600 | 11/1947 | Italy | . |
| 529106 | 11/1940 | United Kingdom | . |

Primary Examiner—Richard A. Bertsch
Assistant Examiner—Howard R. Richman
Attorney, Agent, or Firm—Klaus P. Stoffel

[57] ABSTRACT

Safety glasses for use with an endoscope and similar devices, the glasses being made of a frame, a first lens portion fixed to the frame, a second, moveable lens portion, and a member for connecting the second lens portion to the first lens portion so that the second lens portion is displaceable when an external force is applied against an outer surface of the second lens portion.

9 Claims, 2 Drawing Sheets

SAFETY GLASSES

BACKGROUND OF THE INVENTION

The Present invention relates to safety glasses, and more Particularly to safety glasses worn by a surgeon during endoscopic surgery to prevent the wearer's eyes from being contacted by bodily fluids which might be encountered during an endoscopic procedure.

Endoscopes today are used in a wide variety of procedures which are well known to those in the medical profession. These procedures include passing a long thin optical fiber element through an orifice in the body to permit the endoscopist to view internal parts of the body through the optic fiber. An eyepiece is generally connected to the optical fiber to facilitate viewing by the endoscopist.

It is also generally known in the profession that during an endoscopic procedure bodily fluids of various types can exit around and through the endoscope near the eyepiece so as to splash the endoscopist. Contact between infected bodily fluids and a physician's eye and skin breaks in other surrounding facial parts can transmit any one of a number of maladies, such as Acquired Immune Deficiency syndrome (AIDS), to the physician.

Various devices have been developed to prevent these bodily fluids from contacting the endoscopist. Such devices include those disclosed in U.S. Pat. Nos. 4,848,322 and 4,834,068. Both these patents disclose a relatively large cumbersome shield through which the eyepiece of the endoscope projects in order to prevent infectious fluids from reaching the face of the user.

U.S. Pat. No. 4,958,623 teaches a rubber ring which is attached to the eyepiece of the endoscope and which contacts the eye of the endoscopist to prevent fluids from contacting the eye. This device has the drawback of only providing protection for one eye of the endoscopist.

A more conventional approach which physicians take for eye protection is safety glasses, in order to prevent fluid from contacting the eyes. Safety glasses are preferred by physicians since they generally have larger lenses and provide protection for both eyes as well as considerable portions of the face surrounding the eye. A further advantage of safety glasses is that they are convenient to use as compared to large shields which are placed in front of the entire face.

However, a significant problem with safety glasses worn during endoscopic procedures is not that they fail to provide protection from bodily fluids, but rather they make it very difficult to align the eyepiece of the endoscope with the physicians eye to permit clear unobstructed vision through the endoscope. This problem often results in the physician removing the glasses during the operation to better align the endoscope with his eye. This action of removing the glasses further increases the risk of infection to the physician. Infectious contact can result not only from bodily fluid directly contacting the eyes but also from the physicians hand which might contact a break in his facial skin when removing the glasses.

SUMMARY OF THE INVENTION

Accordingly, it is an object of the present invention to provide safety glasses which permit the eyepiece of the endoscope to be moved toward the eye so as to permit the eyepiece to be aligned with the eye while maintaining eye protection from bodily fluids as would be obtained with conventional safety glasses.

It is a further object to provide glasses of the above type which can be worn for the duration of a surgical procedure, even when the endoscope is not being used.

Pursuant to this object, and others which will become apparent hereafter, one aspect of the present invention resides in safety glasses having at least one lens that can be deflected nearer to the eye of the wearer so that during an endoscopic procedure the eyepiece of the endoscope can be placed against the front of the lens and pushed inward toward the eye of the endoscopist to facilitate alignment of the eye with the eyepiece. The lens is also constructed so that it returns to its original position once the eyepiece is moved away from the wearer's eye.

In a first embodiment of the invention the lens is integral with the frame and is made of a thin clear plastic material which permits a few millimeters of deflection toward the eye.

In yet another embodiment of the invention the lens is made of two pieces and is attached to a frame. The two piece lens includes a clear, relatively rigid central portion which is engageable with the eyepiece of the endoscope. The clear central portion is surrounded by a thin elastic material which connects the central portion to the second piece of the lens which in turn is connected to the frame of the glasses. The elastic material that mounts the clear central portion to the second lens piece permits the central portion to be displaced toward the eye by pressing the endoscope eyepiece against the central portion. Once the eyepiece is taken away from the clear central portion, the central portion is returned to its initial position by the elastic material.

A distinct advantage of the present invention is that it is not cumbersome and it is very easy to use while maintaining protection for the physicians eyes from contact with bodily fluids throughout the entire procedure, even while not using an endoscope, as with conventional safety glasses. The main advantage of the present invention is, however, that it permits a physician to more easily align an endoscope with his eye in a simple manner while maintaining the eye protection. The ability of the lens to deflect inwardly also makes the endoscope easier to use during surgery which as a result makes the procedure itself less strenuous on the physician.

The invention also makes it possible to manufacture the safety glasses very inexpensively so that they are essentially disposable after each use.

The novel features which are considered as characteristic for the invention are set forth in particular in the appended claims. The invention itself, however, both as to its construction and its method of operation, together with additional objects and advantages thereof will be best understood from the following description of specific embodiments when read in connection with the accompanying drawing.

DETAILED DESCRIPTION OF THE PREFERRED EMBODIMENTS

As seen in the figures, the inventive safety glasses are made of a plastic frame 1 and a lens 2 which includes at least one portion 3 that is moveable from a normal position inwardly toward the eye of the wearer.

Figure 1:
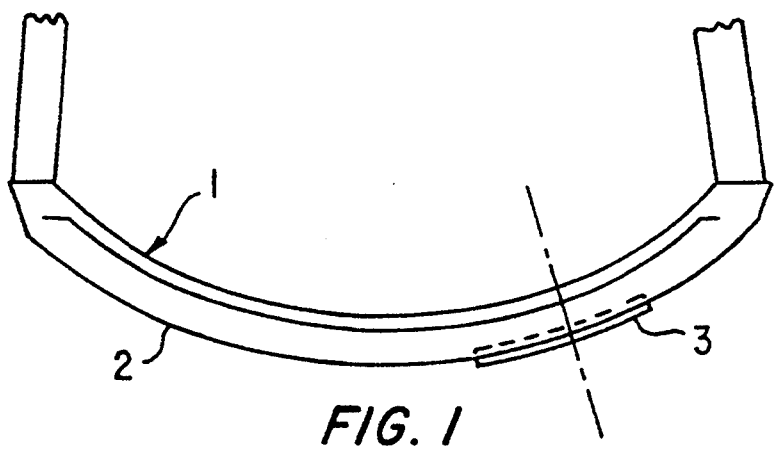
FIG. 1 is a top view of a first embodiment of safety glasses pursuant to the present invention.
Figure 2:
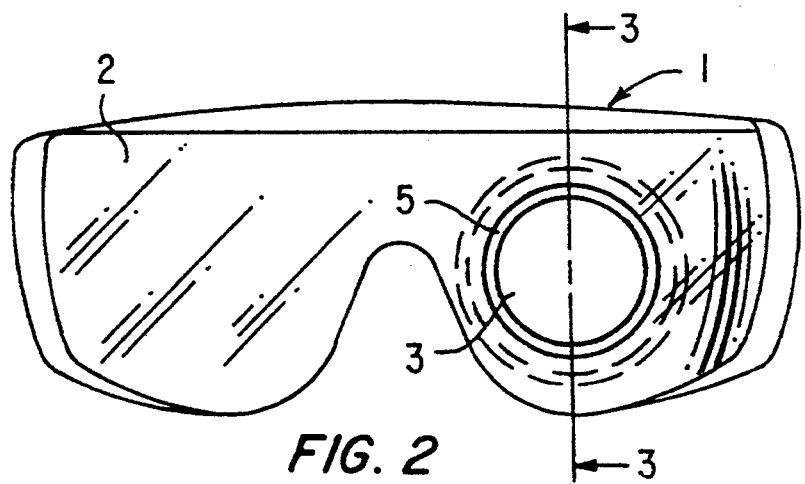
FIG. 2 is a front view of the glasses in FIG. 1.
Figure 3A:
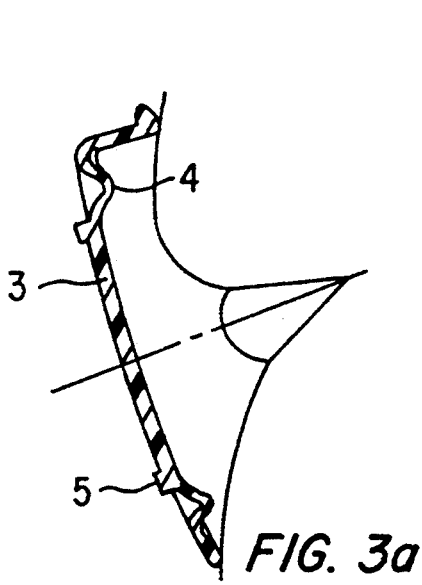
FIG. 3a is a section taken along the line III—III of FIG. 2, with the central lens portion in its normal position.
Figure 3B:
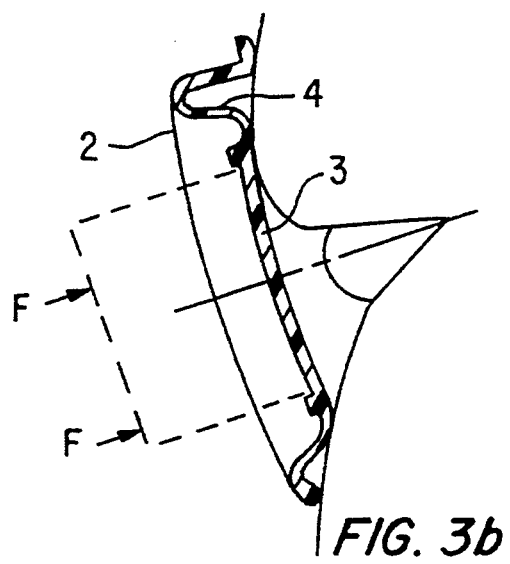
FIG. 3b is a section similar to FIG. 3a, with the central lens portion deflected toward the eye.

As shown in FIG. 2, the moveable portion 3 is shaped so that the wearer can see therethrough without obstruction. In the embodiment of FIGS. 1-3, the frame 1 and the lens 2 are all constructed of the same clear plastic material. The moveable portion 3 is surrounded by an annular portion 4 that has a cross-section, as shown in FIGS. 3a and 3b, which permits the annular portion to act somewhat like a diaphragm. This cross-section is, for example, roughly S-shaped, as shown in FIGS. 3a and 3b, and is composed of the same material as the remainder of the glasses, however it is of a thickness which permits the annular portion 4 to flex when pressure is applied to the external surface the moveable lens portion 3 in the direction of the wearer's eye. This pressure on the external surface of the moveable lens portion 3 is provided, for example, by the eyepiece of an endoscope which is manually moved inward by the physician wearing the glasses. Once the endoscope is removed from the moveable lens portion 3, the moveable lens portion returns to its normal position as shown in FIG. 3a.

An annular ridge 5 can be provided at the perimeter of the moveable lens portion 3 so that the eyepiece of the endoscope fits securely against the moveable lens portion 3 and prevents sliding from side to side.

Figure 4:
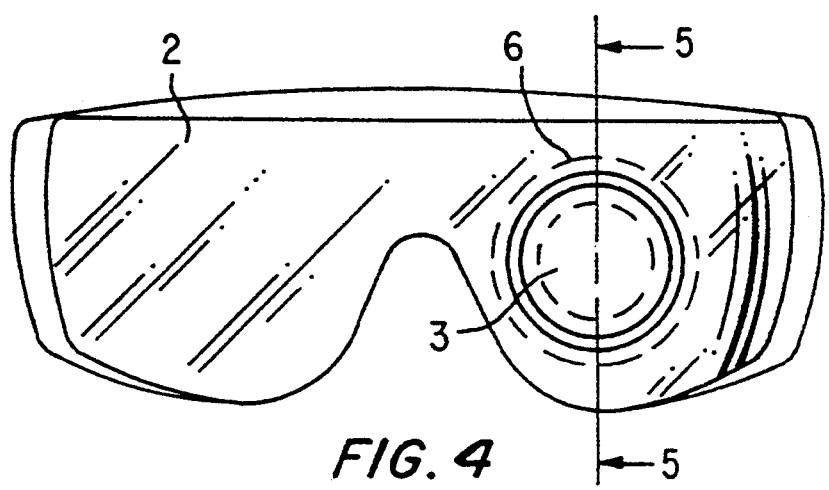
FIG. 4 is a front view of a second embodiment of the invention.
Figure 5A:
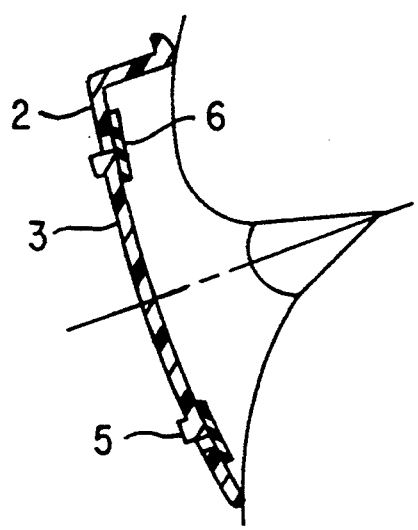
FIG. 5a is a section taken along the line V—V in FIG. 4, showing the central lens portion in its normal position.
Figure 5B:
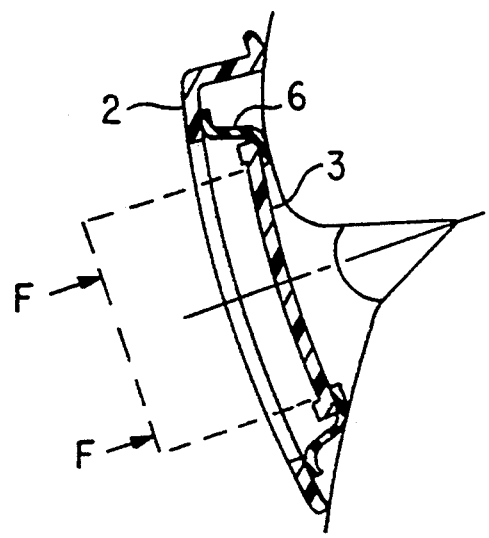
FIG. 5b is a view similar to FIG. 5a showing the central lens portion in a position displaced toward the eye.

FIGS. 4 and 5 illustrate a second embodiment in which the moveable lens portion 3 is connected to the remainder of the lens 2 by an annular elastic member 6. This elastic member 6 can be made of any elastic material which permits up to a few millimeters of deflection of the lens portion 3. Latex rubber is one example of a suitable material. The elastic annulus 6 is glued or fused near its inner circumference to the outer periphery of the lens portion 3. Near its outer circumference the annulus 6 is likewise connected to the main portion of the lens 2. The elastic annulus 6 permits the lens portion 3 to be moved back and forth between its normal position as illustrated in FIG. 5a and a position nearer to the wearer's eye as shown in FIG. 5b. This movement is again caused by a force exerted on the outer surface of the lens portion 3. Once the force is removed, the lens portion 3 returns to its normal position due to the force exerted by the elastic annulus 6. The annulus 6 can be glued to either the outer or inner surfaces of the lens portions 2,3.

Although the embodiments described above only show a single moveable lens portion it is of course possible to provide a moveable lens portion in front of both eyes.

While the invention has been illustrated and described as embodied in safety glasses for endoscopic surgery, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

1. Safety glasses for use with fiber optical surgical devices, comprising:
   a frame;
   a first lens portion fixed to said frame;
   a second lens portion having an inner surface and an outer surface;
   means for connecting said second lens portion to said first lens portion so that said second lens portion is inwardly displaceable toward a wearer's eye when an inwardly directed external force is applied against the outer surface of said second lens portion, said connecting means causing said second lens portion to move outwardly away from the wearer's eye when the external force is removed.

2. Safety glasses as defined in claim 1, wherein said first lens portion has an aperture therein, said second lens portion being arranged within the aperture in said first lens portion.

3. Safety glasses as defined in claim 2, wherein said second lens portion and the aperture in said first lens portion are round.

4. Safety glasses as defined in claim 2, wherein said second lens portion has a continuous ridge on its outer surface near a peripheral edge of said second lens portion, which ridge projects outwardly away from the wearer's eye.

5. Safety glasses as defined in claim 2, wherein said connecting means includes a ring-shaped elastic membrane defining an inner opening, said second lens portion having an outer periphery, said second lens portion being attached near its outer periphery to the elastic membrane so as to cover the inner opening of the ring-shaped membrane, the ring-shaped membrane having an outer periphery connected to said first lens portion.

6. Safety glasses as defined in claim 5, wherein said elastic membrane is made of rubber.

7. Safety glasses as defined in claim 6, wherein said first and second lens portions are glued to the rubber membrane.

8. Safety glasses as defined in claim 2, wherein said connecting means includes an annular diaphragm having an S-shaped cross-section, said second lens portion being connected to an inner perimeter of said diaphragm and an outer perimeter of said diaphragm being connected to said first lens portion, said diaphragm permitting said second lens portion to move between a first normal position and a position displaced inwardly toward a wearer's eye.

9. Safety glasses as defined in claim 8, wherein said frame and said first and second lens portions are made of plastic and have an approximately uniform thickness, said diaphragm also being made of said plastic, and being integral with said frame and said first and second lens portions, and having a thickness that is reduced compared to the thickness of the first and second lens portions so as to permit the S-shaped cross section to flex in response to the external force exerted on the outer surface of said second lens portion, the S-shape acting to oppose the external force so that said second lens portion is returned to the normal position when the force is removed.

* * * * *